United States Patent [19]

Hyatt

[11] Patent Number: 4,621,146

[45] Date of Patent: Nov. 4, 1986

[54] ALKYLTHIOALKYL LACTONES

[75] Inventor: John A. Hyatt, Kingsport, Tenn.

[73] Assignee: Eastman Kodak Company, Rochester, N.Y.

[21] Appl. No.: 811,222

[22] Filed: Dec. 20, 1985

[51] Int. Cl.$^4$ ............................................. C07D 305/12
[52] U.S. Cl. ..................................... 549/263; 549/329
[58] Field of Search ................................. 549/263, 329

[56] References Cited

U.S. PATENT DOCUMENTS 2,585,223  2/1942  Caldwell ............................ 549/329
2,675,392  4/1954  Theobald ........................... 549/263

FOREIGN PATENT DOCUMENTS 51-91  2/1975  Japan ................................... 549/263

OTHER PUBLICATIONS

Houben-Weyl, Methoden der Organischen Chemie, vol. VI/2 (1963), pp. 520-523, 515-517.

Primary Examiner—Norma S. Milestone
Attorney, Agent, or Firm—Donald W. Spurrell; J. Frederick Thomsen

[57] ABSTRACT

Compounds of the formula

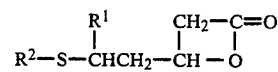

and their preparation wherein $R^1$ and $R^2$ are each selected from H and alkyl wherein the alkyl moieties are straight or branched chain of 1-20 carbons, preferably 1-6 carbons. Readily prepared therefrom are the corresponding unsaturated esters of the formula $R^2S(R^1)CH$—$CH_2$—$CH$=$CH$—COO-alkyl which are useful as intermediates in the preparation of herbicides.

3 Claims, No Drawings

ALKYLTHIOALKYL LACTONES

This invention concerns novel alkylthioalkyl lactones and a markedly improved process for their preparation. The lactones find utility as intermediates in the preparation of herbicides.

The invention more particularly concerns the novel lactone compounds of the formula

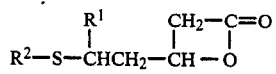

and their preparation wherein $R^1$ and $R^2$ are each selected from H and alkyl wherein the alkyl moieties are straight or branched chain of 1–20 carbons, preferably 1–6 carbons such as methyl, ethyl, propyl, isobutyl, or hexyl. Readily prepared from these lactones are the corresponding unsaturated esters of the formula $R^2S(R^1)CH-CH_2-CH=CH-COO$—alkyl which are useful as intermediates in the preparation of herbicides according to and such as those disclosed in U.K. Pat. No. 2,090,246, incorporated herein by reference.

The present lactones are prepared by contacting an aldehyde of the formula

with ketene at a temperature of from about 0° C. to about 30° C., preferably from about 15° C. to about 25° C., in the presence of a catalytic amount of a Lewis acid catalyst in a low-boiling ether or ester solvent.

In a specific preferred embodiment, the present invention encompasses the compound (I) of the formula

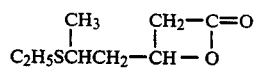

and its manufacture, which compound is employed in the preparation of the herbicide of the formula

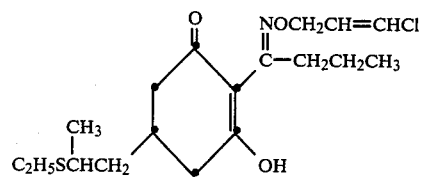

sold under the tradename SELECTONE. This herbicide is prepared, for example, from the above compound (I) by the reaction sequence

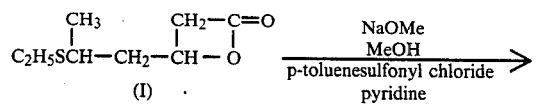

react with $R-OOCCH_2COCH_3 \longrightarrow$

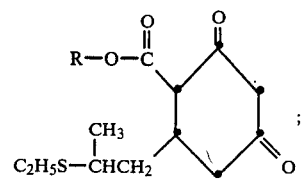

hydrolyze and decarboxylate $\longrightarrow$

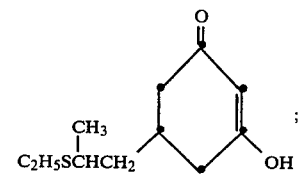

react with $CH_3CH_2CH_2\overset{\overset{O}{\|}}{C}Cl \longrightarrow$

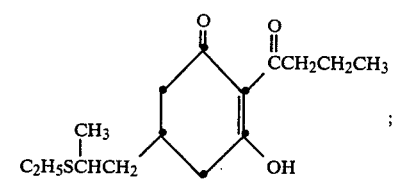

react with $H_2NOCH_2CH=CHCl \longrightarrow$

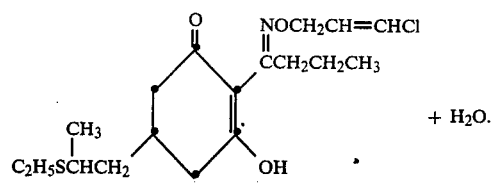

$+ H_2O$.

In accordance with the present invention, ketene is reacted with the aldehyde at about 0° C. to about 30° C. in the presence of a catalytic amount (about 0.35 to about 35 mole % of the total moles of the aldehyde) of a Lewis acid catalyst such as $BF_3$, $BF_3 \cdot Et_2O$, $ZnBr_2$, $ZnI_2$, $FeCl_3$, $MgBr_2$, or the like, in a low-boiling ether or ester solvent such as diethyl ether, tetrahydrofuran, 1,4-dioxane, dipropyl ether, dibutyl ether, ethyl acetate, methyl acetate, dimethoxyethane or the like, according to the equation

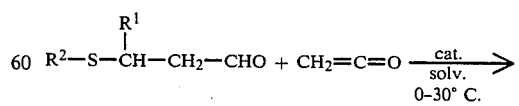

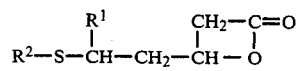

The following examples will further illustrate the invention.

EXAMPLE 1

Preparation of Compound (I)

A solution of 38.6 g (0.288 mole) of distilled 3-(ethylthio)butyraldehyde and 1.5 ml of $BF_3 \cdot Et_2O$ (0.01 moles) in 350 cc of diethyl ether in a round bottom flask equipped with stirrer was stirred at 20° C. on a water bath while ketene gas was added through a frit at such quantity and flow rate as to provide a controlled reaction. After about 1.5 hours, IR analysis of an aliquot showed all aldehyde to be consumed and a strong $\beta$-lactone carbonyl band at 5.5$\mu$. The mixture was purged with $N_2$, washed with 25 ml of saturated aqueous $NaHCO_3$, dried with $MgSO_4$, stripped of ether, and distilled (Kugelrohr 75°-85°/1 mm Hg) to give 36.0 g (72%) of $\beta$-lactone as a clear liquid. Mass spectrum and elemental analysis confirmed the Compound (I) structure.

EXAMPLE 2

Preparation of Intermediate Compound (II) of the Structure

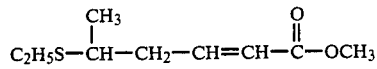

To a solution of 10.0 g (0.0575 mol) of Compound I in 50 ml of methanol in a round bottom flask equipped with stirrer was added 3.19 g (0.0590 mol) of sodium methoxide and the mixture stirred overnight at ambient temperature. The mixture was stripped of methanol and partitioned between ether and water. The organic phase was dried with $MgSO_4$ and stripped of solvent to give 8.4 g (71.2%) of crude $\beta$-hydroxy ester identified by mass spectrum analysis (clear syrup).

A solution of 8.4 g (0.0407 mol) of this crude alcohol in 100 ml of dry pyridine was treated at 20° C. with 7.98 g (0.0420 mol) of p-toluenesulfonyl chloride and the mixture stirred at room temperature for 2.5 hours. The reaction mixture was then heated on the steam bath to about 70° C. for 3 hours and let stand at room temperature overnight. The reaction mixture was poured into water, extracted with ethyl acetate, washed with 10% HCl and then with water, dried with $MgSO_4$ and stripped of ethyl acetate. The residue was distilled in a short-path apparatus to give 5.03 g (65.6%) of the desired Compound (II) identified by mass spectrum analysis.

The invention has been described in detail with particular reference to preferred embodiments thereof, but it will be understood that variations and modifications will be effected within the spirit and scope of the invention.

I claim:

1. A compound of the formula

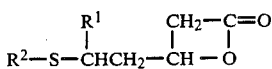

wherein $R^1$ and $R^2$ are each selected from H and alkyl of 1-20 carbons.

2. A compound according to claim 1 wherein $R^1$ and $R^2$ are each selected from alkyl of 1-6 carbons.

3. The compound according to claim 1 of the formula

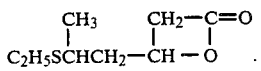

* * * * *